United States Patent
Fetzer et al.

(10) Patent No.: US 9,304,114 B2
(45) Date of Patent: Apr. 5, 2016

(54) ULTRASONIC INSPECTION USING INCIDENCE ANGLES

(71) Applicant: The Boeing Company, Chicago, IL (US)

(72) Inventors: Barry Allen Fetzer, Renton, WA (US); Kate Brown Boudreau, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 350 days.

(21) Appl. No.: 13/860,687

(22) Filed: Apr. 11, 2013

(65) Prior Publication Data

US 2014/0305220 A1    Oct. 16, 2014

(51) Int. Cl.
*G01N 29/36* (2006.01)
*G01N 29/26* (2006.01)
*G10K 11/34* (2006.01)

(52) U.S. Cl.
CPC .............. *G01N 29/36* (2013.01); *G01N 29/262* (2013.01); *G01N 2291/044* (2013.01); *G01N 2291/056* (2013.01); *G10K 11/346* (2013.01)

(58) Field of Classification Search
CPC ............ G01N 29/36; G01N 2291/044; G01N 29/262; G01N 2291/056; G10K 11/346
USPC .......................................................... 73/629
See application file for complete search history.

(56) References Cited

U.S. PATENT DOCUMENTS

| 7,293,461 | B1* | 11/2007 | Girndt .............................. 73/622 |
| 2004/0016299 | A1* | 1/2004 | Glascock et al. ............... 73/638 |
| 2009/0277269 | A1* | 11/2009 | Sarr ................................. 73/620 |
| 2010/0046576 | A1* | 2/2010 | Desai ............................. 374/119 |
| 2010/0242613 | A1* | 9/2010 | Simard ................ G01N 29/262 73/641 |
| 2010/0246326 | A1* | 9/2010 | Ichigo et al. .................... 367/93 |
| 2011/0166807 | A1* | 7/2011 | Kitazawa et al. ............... 702/56 |
| 2011/0247417 | A1* | 10/2011 | Oberdoerfer et al. .......... 73/598 |

FOREIGN PATENT DOCUMENTS

| EP | 1043584 A1 | 10/2000 |
| JP | 2007322350 A | 12/2007 |
| WO | WO2010026253 A1 | 3/2010 |

OTHER PUBLICATIONS

Partial International Search Report, dated Jul. 28, 2014, regarding Application No. PCT/US2014/028510, 5 pages.
International Search Report and Written Opinion, dated Nov. 11, 2014, regarding Application No. PCT/US2014/028510, 15 pages.

* cited by examiner

*Primary Examiner* — J M Saint Surin
(74) *Attorney, Agent, or Firm* — Yee & Associates, P.C.

(57) ABSTRACT

A method and apparatus is presented. A signal may be sent into a structure at an incidence angle from a transducer array. A response signal reflected from the structure in response to the signal sent into the structure may be detected at the transducer array to form a received response.

26 Claims, 7 Drawing Sheets

FIG. 9 ical embodiments are set forth in the appended claims. The illus-

ULTRASONIC INSPECTION USING INCIDENCE ANGLES

BACKGROUND INFORMATION

1. Field

The present disclosure relates generally to ultrasonic inspection and, in particular, to a method and apparatus for identifying undesirable conditions in an object using ultrasonic inspection. Still more particularly, the present disclosure relates to a method and apparatus for ultrasonic inspection using signals with an incidence angle.

2. Background

Aircraft are being designed and manufactured with greater and greater percentages of composite materials. Some aircraft may have more than fifty percent of its primary structure made from composite materials. Composite materials may be used in aircraft to decrease the weight of the aircraft. This decreased weight may improve payload capacities and fuel efficiencies. Further, composite materials may provide longer service life for various components in an aircraft.

Composite materials may be tough, light-weight materials created by combining two or more dissimilar components. For example, a composite may include fibers and resins. The fibers and resins may be combined to form a cured composite material.

In particular, key components, such as wings and fuselage skins, may be constructed with composite materials such as, without limitation, a composite laminate. With more and more critical structures being made of composite laminates, methods and techniques to assure that these components meet quality standards are needed more than ever before.

The presence of foreign materials or debris within a composite component is an example of a known undesirable condition that may occur during processing to create composite components. Currently, much time, effort, and money may be spent on non-destructive measurement systems designed to detect and quantify the debris in composite components, such as those made using carbon laminates. Other examples of undesirable conditions include, for example, porosity within the component and delamination.

Ultrasonic testing involves sending ultrasonic pulse waves into an object to detect undesirable conditions or to characterize materials. In ultrasonic testing, one or more ultrasound transducers are passed over an object that is being inspected. The transducers are typically separated from the test object by a coupling material. This coupling material may be, for example, a liquid such as oil or water. The coupling material is used to prevent signal loss. In this manner, undesirable conditions may be detected.

However, identification of debris may be difficult using one transducer for ultrasonic testing. Further, ultrasonic inspection using more than one ultrasound transducer may be undesirably difficult to control or implement.

Therefore, it would be desirable to have a method and apparatus that take into account at least some of the issues discussed above, as well as other possible issues.

SUMMARY

In an illustrative embodiment, a method may be provided. A signal may be sent into a structure at an incidence angle from a transducer array. A response signal reflected from the structure in response to the signal sent into the structure may be detected at the transducer array to form a received response.

In another illustrative embodiment, an apparatus may comprise a transducer array comprising a plurality of elements. A number of sending elements in the plurality of elements may be configured to send a signal into a structure at an incidence angle. A number of receiving elements in the plurality of elements may be configured to detect a response signal reflected from a back surface of the structure.

In a further illustrative embodiment, a method may be provided. A first location of a transducer array may be identified based on an incidence angle, a thickness, and a material velocity. A second location of the transducer array may be identified based on the incidence angle, the thickness, and the material velocity. The transducer array may be configured using the first location and the second location. Configuring the transducer array may comprise configuring the transducer array to have receiving elements at the first location and configuring the transducer array to have inactive elements at the second location. A signal may be sent into a composite material at an incidence angle using sending elements of the transducer array. A response signal reflected from a back surface of the composite material may be detected using the receiving elements. An inconsistency within the composite material may be identified using the response signal.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account different considerations. For example, the different illustrative embodiments recognize and take into account that traditionally the same ultrasound transducer may send ultrasound signals normal to the object and receive ultrasound signals. The different illustrative embodiments also recognize and take into account that when using the same ultrasound transducer and signals normal to the object, the reflection from debris may closely match the reflection from the material. As a result, identification of debris may be difficult.

Likewise, the different illustrative embodiments recognize and take into account that one ultrasound transducer may be used to transmit the ultrasound signals through the surface using an angled wedge while a separate receiver detects a response from the other surface after travelling through a medium. The different illustrative embodiments recognize and take into account that using more than one ultrasonic transducer may require alignment and may be larger than using the same transducer, increasing the difficulty of control and implementation.

Additionally, the different illustrative embodiments recognize that by not detecting response signals reflected from inconsistencies, the signal to noise ratio may be increased. The different illustrative embodiments also recognize that sensitivity may be increased by not detecting response signals reflected from inconsistencies. The different illustrative embodiments recognize and take into account that by not detecting response signals reflected from inconsistencies inspection time may be decreased. The different illustrative embodiments further recognize and take into account that by increasing the sensitivity, inspections of more complex structures may be performed.

Thus the different illustrative embodiments provide a method and apparatus for identifying undesirable conditions in an object using ultrasonic inspection. In one illustrative example, a signal may be sent into a structure at an incidence angle from a transducer array. A response signal reflected from the structure at the transducer array in response to the signal sent into the structure may be detected to form a received response.

Figure 1:
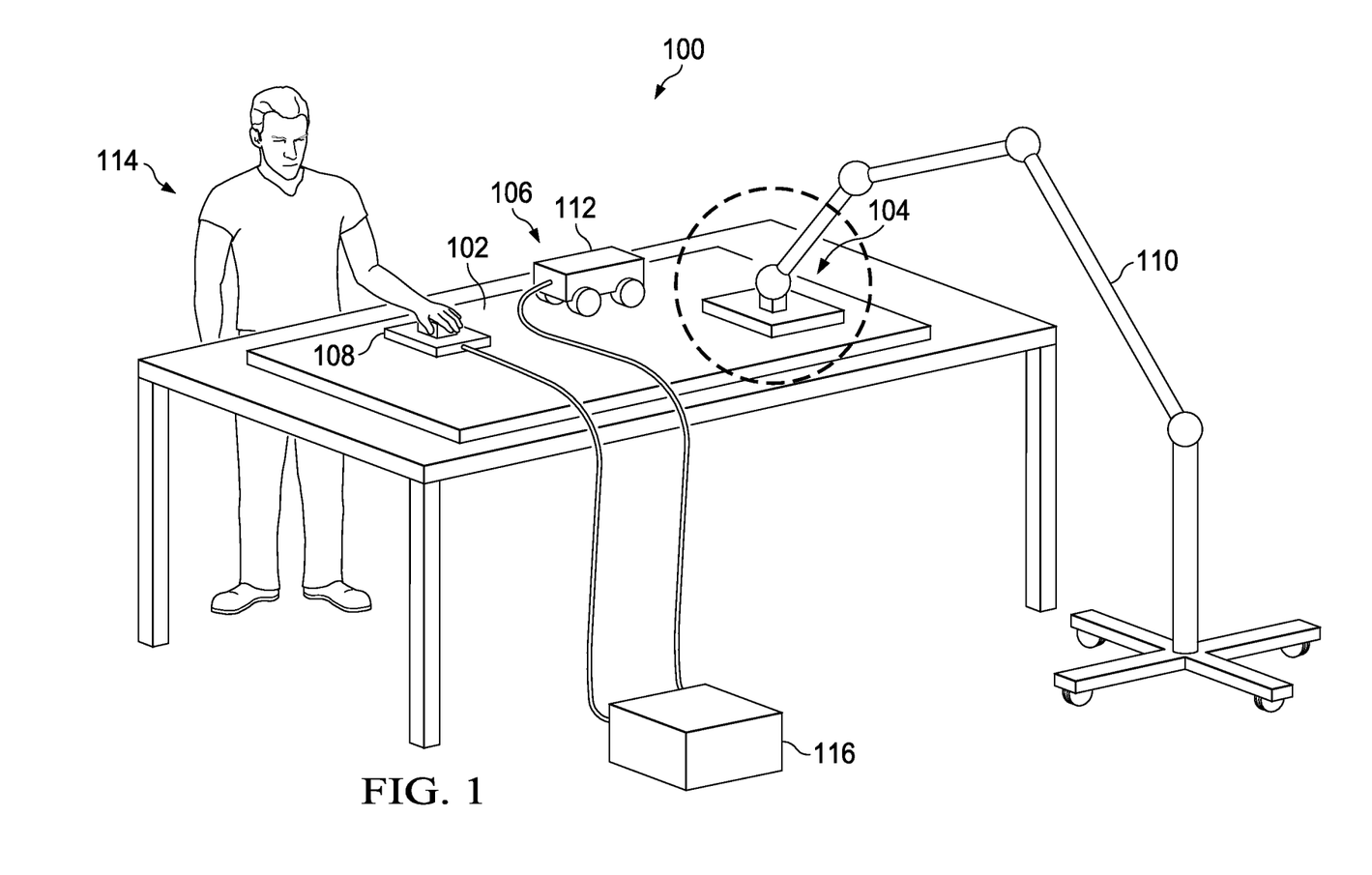
FIG. 1 is an illustration of a production environment in which an illustrative embodiment may be implemented.

With reference now to the figures, and in particular, with reference to FIG. 1, an illustration of a production environment is depicted in accordance with an illustrative embodiment. In this illustrative embodiment, production environment 100 has structure 102. Structure 102 may be comprised of a number of different materials. These materials may include, for example, without limitation, plastic, metal, composite material, ceramics, and other suitable types of materials. As depicted, structure 102 may be a composite panel.

Production environment 100 also has inspection equipment 104, inspection equipment 106, and inspection equipment 108. As depicted, inspection equipment 104 may be moved along structure 102 by articulated arm 110. As depicted, inspection equipment 106 may be moved along structure 102 by crawler robot 112. As depicted, inspection equipment 108 may be moved along structure 102 by human operator 114.

Each of inspection equipment 104, inspection equipment 106, and inspection equipment 108 may be associated with a water source to provide a coupling material for inspection. As depicted, inspection equipment 104 may receive water from utility conduits associated with articulated arm 110. As depicted, inspection equipment 106 and inspection equipment 108 may be coupled to a utility source 116 using respective utility conduits.

This illustration of production environment 100 is provided for purposes of illustrating one environment in which the different illustrative embodiments may be implemented. The illustration of production environment 100 in FIG. 1 is not meant to imply architectural limitations as to the manner in which different illustrative embodiments may be implemented. For example, only one of human operator 114, crawler robot 112, and articulating arm 110 may be present in production environment 100. Further, structure 102 need not be a composite panel. In one illustrative example, structure 102 may be a metallic panel. In another illustrative example, structure 102 may be a composite stiffener. In yet another illustrative example, structure 102 may be a fuselage section of an aircraft. Yet further, structure 102 need not be supported by a table as depicted.

Figure 2:
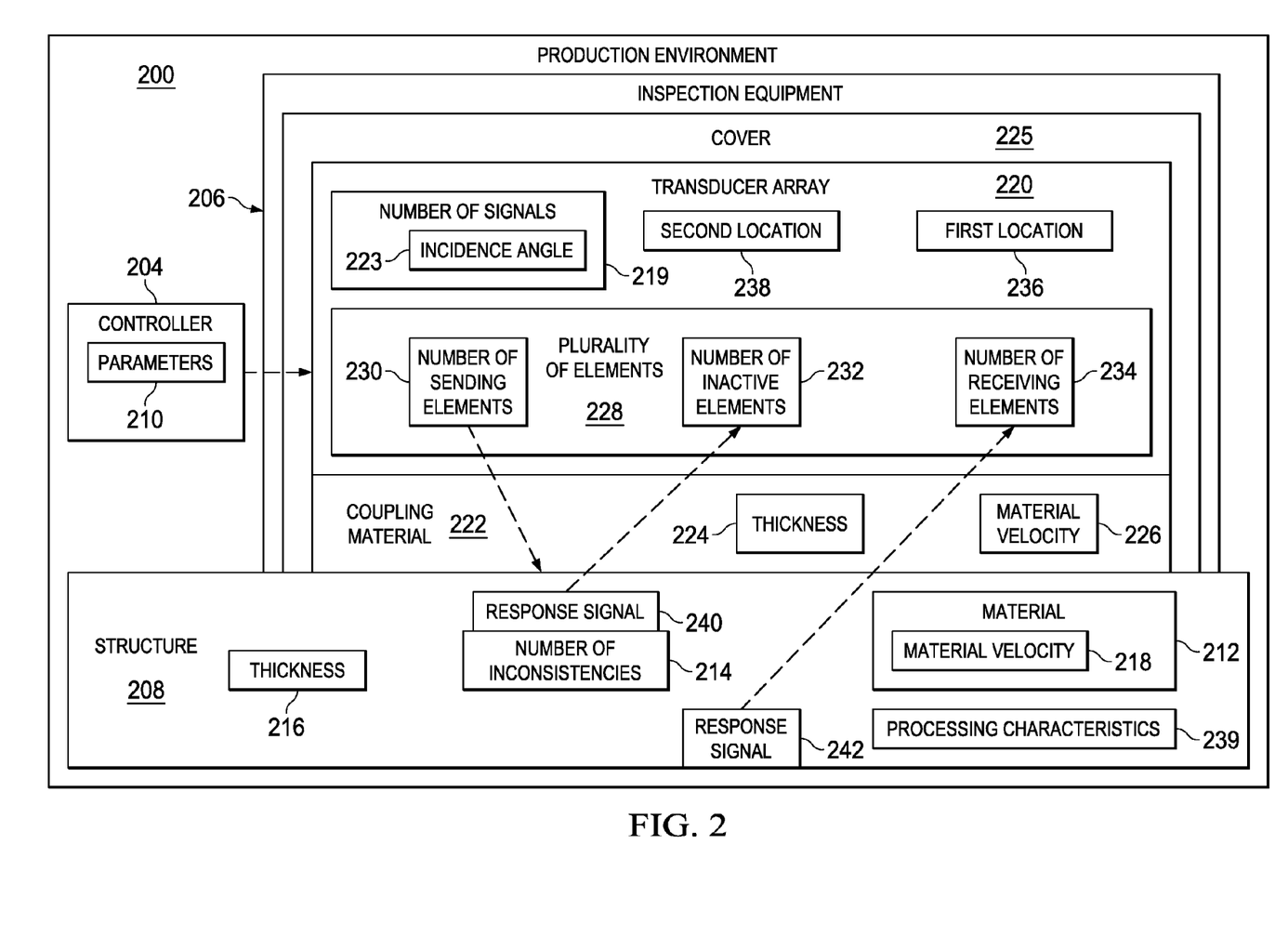
FIG. 2 is an illustration of a production environment in the form of a block diagram in accordance with an illustrative embodiment.

Turning now to FIG. 2, an illustration of a production environment in the form of a block diagram is depicted in accordance with an illustrative embodiment. Production environment 200 may be one implementation of production environment 100 of FIG. 1.

Production environment 200 comprises controller 204, inspection equipment 206, and structure 208. Controller 204 may be configured to control inspection of structure 208 by inspection equipment 206 using number of parameters 210. Number of parameters 210 may comprise at least one of amplitude, number of pulses, incidence angle, or other suitable parameters. As used herein, the phrase "at least one of," when used with a list of items, means different combinations of one or more of the listed items may be used, and only one of each item in the list may be needed. For example, "at least one of item A, item B, and item C" may include, without limitation, item A, item A and item B, or item B. This example also may include item A, item B, and item C or item B and item C. In other examples, "at least one of" may be, for example, without limitation, two of item A, one of item B, and ten of item C; four of item B and seven of item C; and other suitable combinations. The item may be a particular object, thing, or a category. In other words, at least one of means any combination of items and number of items may be used from the list but not all of the items in the list are required.

Further, controller 204 may be used to configure inspection equipment 206. Controller 204 may be implemented in software, hardware, firmware or a combination thereof. When software is used, the operations performed by controller 204 may be implemented in program code configured to run on a processor unit. When firmware is used, the operations performed by controller 204 may be implemented in program code and data and stored in persistent memory to run on a processor unit. When hardware is employed, the hardware may include circuits that operate to perform the operations in controller 204.

Inspection equipment 206 is configured to inspect structure 208. Structure 208 comprises material 212, number of inconsistencies 214, and thickness 216. Material 212 has material velocity 218. Material velocity 218 is a measure of the speed at which signals propagate in material 212.

Inspection equipment 206 may identify number of inconsistencies 214 through inspection of structure 208. As used herein, a "number of" items means one or more items. For example, number of inconsistencies 214 means one or more inconsistencies. Number of inconsistencies 214 comprises a number of undesirable conditions within structure 208. Number of inconsistencies 214 may include foreign material, debris, voids, or other suitable undesirable conditions.

Inspection equipment 206 may send signals through coupling material 222 and into structure 208. Coupling material 222 may be used to increase the transmission of number of signals 219 into structure 208. Coupling material 222 has thickness 224 and material velocity 226. Material velocity 226 is a measure of the speed at which signals propagate in coupling material 222. In some illustrative examples, material velocity 226 may be different than material velocity 218. The difference between material velocity 226 and material velocity 218 is smaller than the difference between the velocity of air and material velocity 218. Accordingly, coupling material 222 reduces the reflection which would occur if air were between transducer array 220 and structure 208. Coupling material 222 may be one of an oil, a gel, a hydrogel, water, or other suitable materials. Coupling material 222 may be selected based on material velocity 218, material velocity 226, inactivity with material 212, cost, or other suitable parameters.

Inspection equipment 206 may inspect structure 208 by sending number of signals 219 into structure 208 using transducer array 220. Transducer array 220 is held within cover 225 and comprises plurality of elements 228. Plurality of elements 228 comprises number of sending elements 230, number of inactive elements 232, and number of receiving elements 234. Controller 204 may configure inspection equipment 206 by configuring each of plurality of elements 228 of transducer array 220 to be one of number of sending elements 230, number of inactive elements 232, or number of receiving elements 234. Controller 204 may configure plurality of elements 228 based on at least one of incidence angle 223 of number of signals 219 to be sent, thickness 216, material velocity 218 of material 212, thickness 224 of coupling material 222, material velocity 226 of coupling material 222, or any other suitable parameter. In some illustrative examples, controller 204 may configure transducer array 220 based on second location 238 and first location 236.

Number of sending elements 230 is configured to send number of signals 219 into structure 208. In some illustrative examples, transducer array 220 may send number of signals 219 at incidence angle 223. Incidence angle 223 may be any desirable angle as long as response signal 242 reflected from back surface of structure 208 would reach transducer array 220. In one illustrative example, incidence angle 223 may be 6 degrees.

In some illustrative examples, number of sending elements 230 may send number of signals 219 at incidence angle 223 using electronic time-delay beam steering or other suitable methods. By sending number of signals 219 from transducer array 220 at incidence angle 223 using electronic time-delay beam steering, transducer array 220 may remain parallel to structure 208.

Number of inactive elements 232 are not configured to send or receive signals. As a result, responses reaching number of inactive elements 232 will not be detected. By not detecting response signal 240 reflected from number of inconsistencies 214, ultrasound inspection may be improved.

In some illustrative examples, number of inactive elements 232 may be located at second location 238. In some illustrative examples, only some inactive elements of number of inactive elements 232 may be located at second location 238. In some illustrative examples, second location 238 of transducer array 220 may be identified based on at least one of incidence angle 223, thickness 224, thickness 216, material velocity 226, and material velocity 218. In some illustrative examples, second location 238 may be an estimated receiving location for response signal 240 reflected from an inconsistency of number of inconsistencies 214 within structure 208. In some illustrative examples, second location 238 may be determined based on processing characteristics 239 of structure 208. Examples of processing characteristics 239 may be likely chemical composition of number of inconsistencies 214 during processing of structure 208, layers of structure 208 most susceptible to inconsistencies during processing of structure 208, and other suitable processing characteristics.

Number of inactive elements 232 may increase sensitivity of ultrasound inspection for detecting inconsistencies 214. If response signal 240 reaches number of inactive elements 232, response signal 240 will not be detected. By not detecting response signal 240 reflected from number of inconsistencies 214, ultrasound inspection may be improved.

Ultrasound inspection may be improved by decreasing the amplitude of response signal 242 relative to number of inconsistencies 214. In other words, amplitude of response signal 242 will be greater when an inconsistency in number of inconsistencies 214 is not present in the tested area of structure 208. The amplitude of response signal 242 will be smaller when an inconsistency in number of inconsistencies 214 is present in the tested area of structure 208.

In some illustrative examples, number of inactive elements 232 is configured to decrease an amplitude of response signal 242 reflected from the back surface of structure 208 when an inconsistency in number of inconsistencies 214 is present. In some illustrative examples, incidence angle 223 is configured to decrease an amplitude of response signal 242 reflected from the back surface of structure 208 when an inconsistency is present.

An inconsistency in number of inconsistencies 214 may be identified by subtracting amplitude of response signal 242 from a desired value. The desired value may be the amplitude of a response signal reflected from the back wall of structure 208 when an inconsistency in number of inconsistencies 214 is not present.

By not detecting response signal 240 reflected from number of inconsistencies 214, the difference in amplitude may be greater. Further, by not detecting response signal 240 reflected from number of inconsistencies 214, the difference in amplitude may be more easily identified. Further, by not detecting response signal 240 reflected from number of inconsistencies 214, the difference in amplitude may be identified more quickly.

Thus, by increasing the signal loss relative to the presence of an inconsistency in number of inconsistencies 214, the sensitivity of ultrasound inspection to number of inconsistencies 214 may be increased. By increasing sensitivity, inspection times may be reduced. Yet further, increasing sensitivity may allow for more complex structures to be inspected.

Number of receiving elements 234 are configured to detect response signal 242 reflected from structure 208 in response to a signal of number of signals 219 sent into the structure 208 to form a received response. Transducer array 220 may be configured such that number of receiving elements 234 is located at first location 236. First location 236 may be located at an estimated receiving location for response signal 242 reflected from the back surface of structure 208. First location 236 of transducer array 220 may be identified based on at least one of incidence angle 223, thickness 224, thickness 216, material velocity 226, or material velocity 218.

In some illustrative examples, second location 238 may be determined based on first location 236. In these illustrative examples, second location 238 may be the area of transducer array 220 between number of sending elements 230 and first location 236.

As depicted in FIG. 2, by sending number of signals 219 at incidence angle 223, response signal 240 and response signal 242 return at non-normal angles. Due to the location of number of inconsistencies 214 within structure 208, response signal 240 reflected from number of inconsistencies 214 will reach transducer array 220 at a different location than response signal 242. By sending number of signals 219 at incidence angle 223, inspection equipment increases the difference in distance traveled by response signal 240 and response signal 242. This difference in distance is greater than if number of signals 219 were sent in a direction normal to structure 208. Accordingly, the difference between the time response signal 240 is received and the time response signal 242 is received is also increased when compared to sending number of signals 219 in a direction normal to structure 208. This increase in time difference may also increase one of sensitivity and the signal to noise ratio.

The illustration of production environment 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in some illustrative examples, transducer array 220 may not have second location 238. Number of inactive elements 232 may be located in transducer array 220 based on not being one of number of sending elements 230 or number of receiving elements 234.

Figure 3:
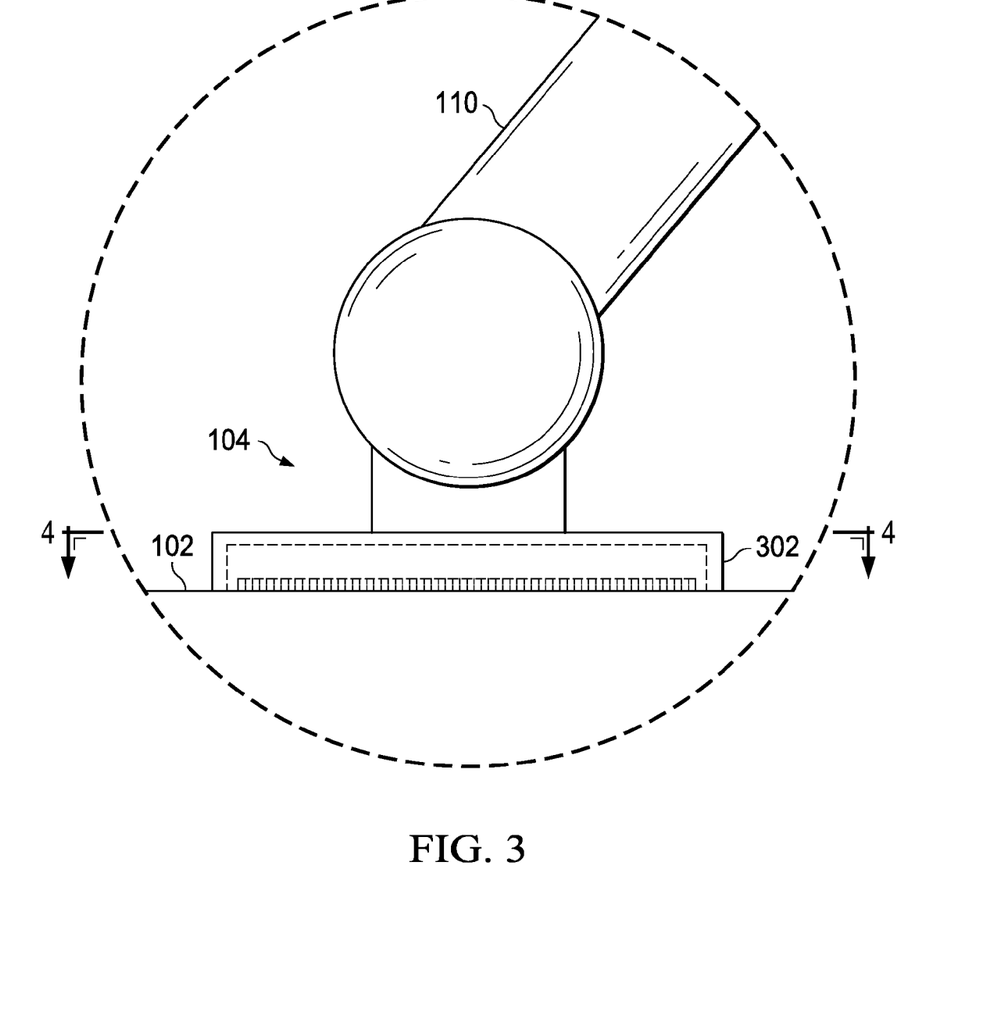
FIG. 3 is an illustration of inspection equipment within a production environment in accordance with an illustrative embodiment.

Turning now to FIG. 3, an illustration of inspection equipment within a production environment is depicted in accordance with an illustrative embodiment. FIG. 3 is a detailed view of inspection equipment 104 on structure 102 of FIG. 1.

As depicted, articulated arm 110 holds inspection equipment 104. Articulated arm 110 may move inspection equipment 104 across structure 102. Inspection equipment 104 has cover 302. Cover 302 may be pressed against structure 102 as inspection equipment 104 is moved across structure 102.

Figure 4:
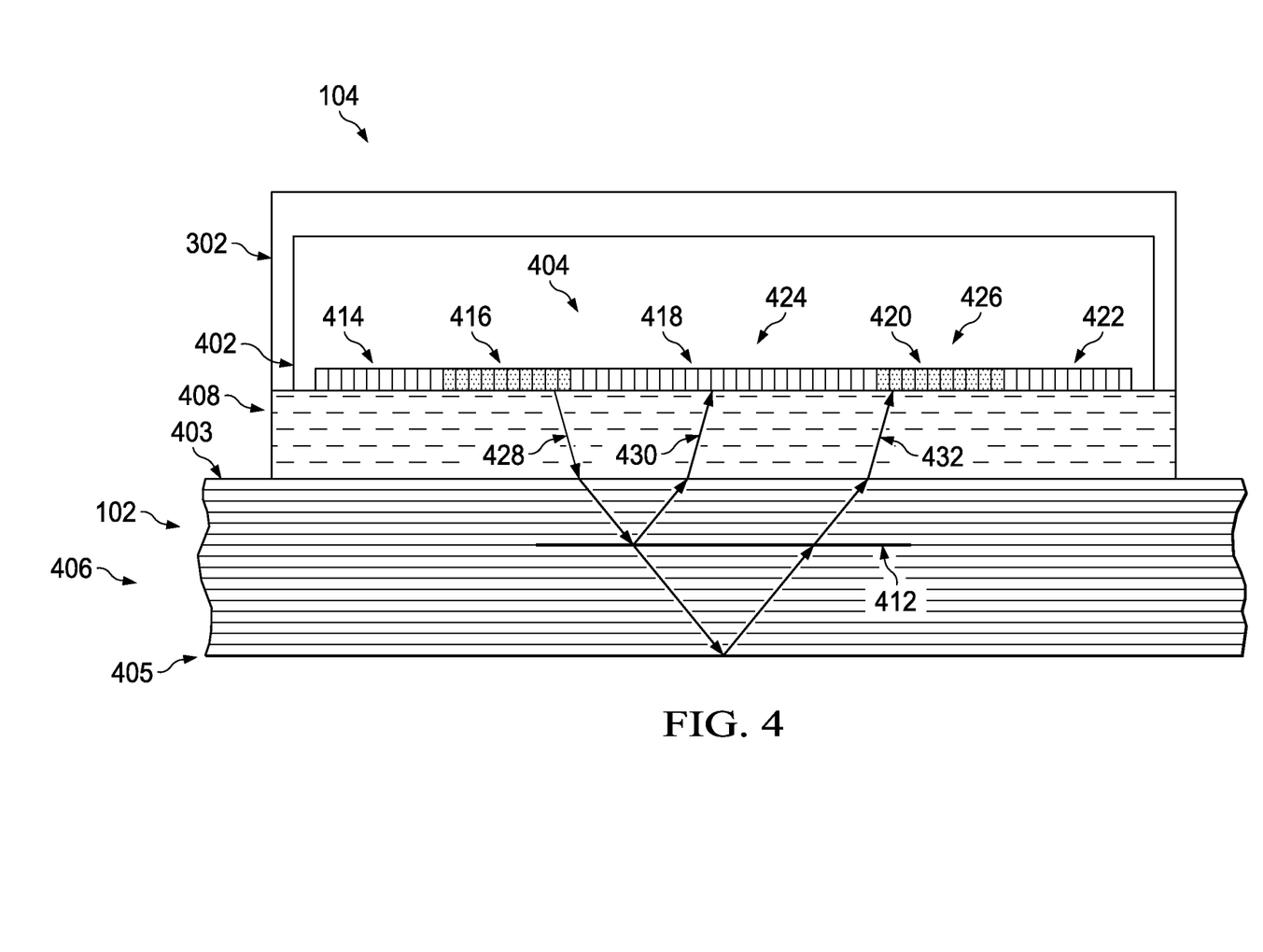
FIG. 4 is an illustration of a cross-sectional view of inspection equipment within a production environment in accordance with an illustrative embodiment.

Turning now to FIG. 4, an illustration of a cross-sectional view of inspection equipment within a production environment is depicted in accordance with an illustrative embodiment. FIG. 4 is a cross-sectional view of inspection equipment 104 on structure 102 of FIG. 1 and FIG. 3, taken along lines 4-4 in FIG. 3.

Inspection equipment 104 is configured to identify inconsistency 412 in structure 102. Inspection equipment 104 has cover 302 and transducer array 402. Transducer array 402 has plurality of elements 404. Transducer array 402 is configured to send signals into structure 102. Structure 102 has front surface 403, back surface 405, plurality of layers of material 406, and inconsistency 412. Transducer array 402 may send signals through coupling material 408 and front surface 403 into structure 102. As depicted, coupling material 408 may comprise water.

Plurality of elements 404 may be a physical implementation of plurality of elements 228 of FIG. 2. Plurality of elements 404 comprises inactive elements 414, sending elements 416, inactive elements 418, receiving elements 420, and inactive elements 422. Plurality of elements 404 may comprise any number of elements. As depicted, plurality of elements 404 comprises 64 elements. By increasing the number of elements in plurality of elements 404 of transducer array 402, transducer array 402 may achieve a higher resolution. By decreasing the number of elements in plurality of elements 404 of transducer array 402, transducer array 402 may achieve a lower resolution.

As depicted, inactive elements 418 are located at second location 424 of transducer array 402. Receiving elements 420 are located at first location 426.

In operation, sending elements 416 may send signal 428 at an incident angle through coupling material 408 and into structure 102. As depicted, some of signal 428 will reflect off inconsistency 412 as response signal 430. As depicted, response signal 430 will reach transducer array 402 at inactive elements 418. Accordingly, response signal 430 will not be detected by transducer array 402.

The remainder of signal 428 may continue to back surface 405 of structure 102. The remainder of signal 428 may reflect off back surface 405 as response signal 432. As depicted, response signal 432 will reach transducer array 402 at receiving elements 420. Accordingly, response signal 432 will be detected by transducer array 402.

By not detecting response signal 430, the sensitivity of the inspection by transducer array 402 may be greater than an inspection using signals normal to structure 102. Increased sensitivity may result in faster evaluation times. Further, increased sensitivity may allow transducer array 402 to inspect more complex structures than could be inspected using signals normal to the structure. Yet further, by not detecting response signal 430, the signal to noise ratio of the inspection by transducer array 402 may be greater than by using signals normal to structure 102.

In FIG. 1 and FIGS. 3-4, illustrations of an inspection system are depicted in accordance with an illustrative embodiment. The different components shown in FIG. 1 and FIGS. 3-4 for inspection equipment 104 may be combined with components in FIG. 2, used with components in FIG. 2, or a combination of the two. Additionally, some of the components in these figures may be illustrative examples of how components shown in block form in FIG. 2 may be implemented as physical structures.

Figure 5:
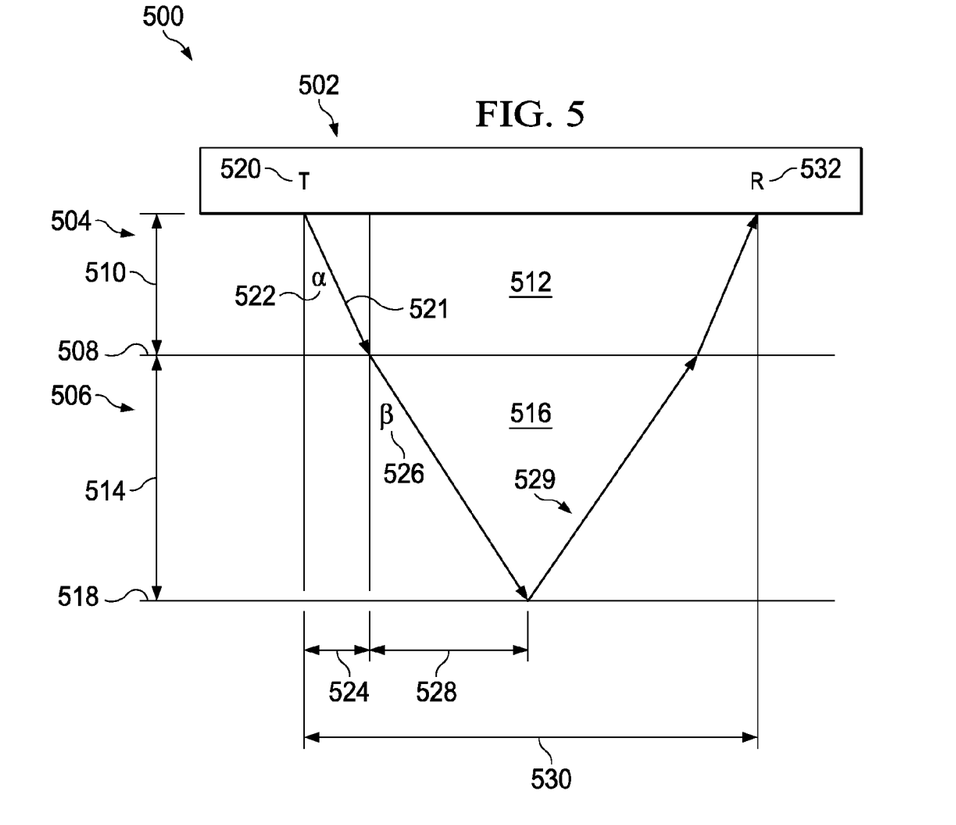
FIG. 5 is an illustration of a method of identifying a first location in accordance with an illustrative embodiment.

Turning now to FIG. 5, an illustration of a method of identifying a first location is depicted in accordance with an illustrative embodiment. As depicted, FIG. 5 is an illustration representing a process of calculating first location 236 of FIG. 2.

Testing environment 500 comprises transducer array 502, coupling material 504, and structure 506. Structure 506 has front surface 508 and back surface 518. As depicted, coupling material 504 has thickness 510 and material velocity 512. As depicted, structure 506 has thickness 514 and material velocity 516.

To identify first location 532, a calculation may be based on signals being sent from third location 520. Signal 521 may be sent at incidence angle 522. Signal 521 may travel distance 524 prior to reaching front surface 508.

Distance 524 may be determined by any suitable method. In one illustrative example, distance 524 may be determined according to the following formula: $X1=Y1*\tan \alpha$, wherein X1 represents distance 524, Y1 represents thickness 510, and $\alpha$ represents incidence angle 522.

Upon reaching front surface 508, an angle of signal 521 relative to front surface 508 may change from incidence angle 522 to angle 526. The angle of signal 521 may change at front surface 508 as a result of the difference in value between material velocity 512 and material velocity 516. Angle 526 may be determined by any suitable method. In one illustrative example, angle 526 may be determined according to the following formula: $\beta=\arcsin((v2/v1)*\sin \alpha)$, wherein v2 represents material velocity 516, v1 represents material velocity 512, and $\beta$ represents angle 526.

Signal 521 may travel distance 528 as signal 521 travels from front surface 508 to back surface 518. Distance 528 may be determined by any suitable method. In one illustrative example, distance 528 may be determined according to the following formula: $X2=Y2*\tan \beta$, wherein X2 represents distance 528 and Y2 represents thickness 514.

Upon reaching back surface 518, signal 521 may reflect off back surface 518. Signal response 529 produced may be substantially the same angle as angle 526. Signal response 529 may then travel through structure 506 towards front surface 508. Upon reaching front surface 508, the angle of signal response 529 may change. The angle of signal response 529 may change at front surface 508 as a result of the difference in value between material velocity 512 and material velocity 516. The angle of signal response 529 may be substantially the same angle as incidence angle 522.

Signal response 529 may then travel through coupling material 504 towards transducer array 502. Signal response 529 may then reach structure 506 at first location 532. First location 532 may be described as an estimated receiving location for a response reflected from back surface 518 of structure 506.

Distance 530 comprises a total traversed distance from third location 520 to first location 532. Distance 530 may be determined by any suitable method. Distance 530 may be expressed as twice the sum of distance 524 and distance 528. In one illustrative example, distance 530 may be determined according to the following formula: $X3=2*((Y1*\tan\alpha)+(Y2*\tan(\arcsin((v2/v1)*\sin\alpha))))$, wherein X3 represents distance 530. Distance 530 and third location 520 may be used to identify first location 532.

Figure 6:
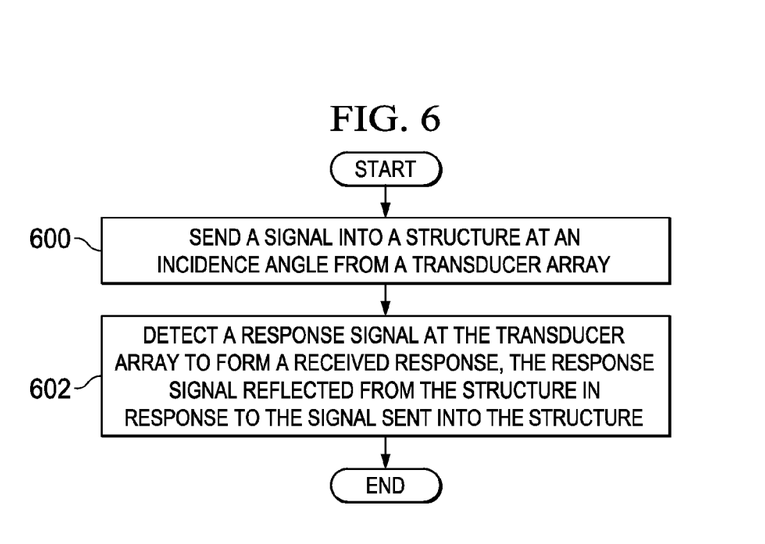
FIG. 6 is an illustration of a process for inspecting a structure in accordance with an illustrative embodiment.

Turning now to FIG. 6, an illustration of a process for inspecting a structure is depicted in accordance with an illustrative embodiment. The process illustrated in FIG. 5 may be implemented using inspection equipment 206 of FIG. 2. Further, this process may be implemented to inspect structure 208 for number of inconsistencies 214 in FIG. 2.

The process may begin by sending a signal into a structure at an incidence angle from a transducer array (operation 600). The signal may be directed at an incidence angle by electronic time-delay beam steering. The process may then detect a response signal at the transducer array to form a received response, the response signal reflected from the structure in response to the signal sent into the structure (operation 602). Afterwards the process terminates.

Figure 7:
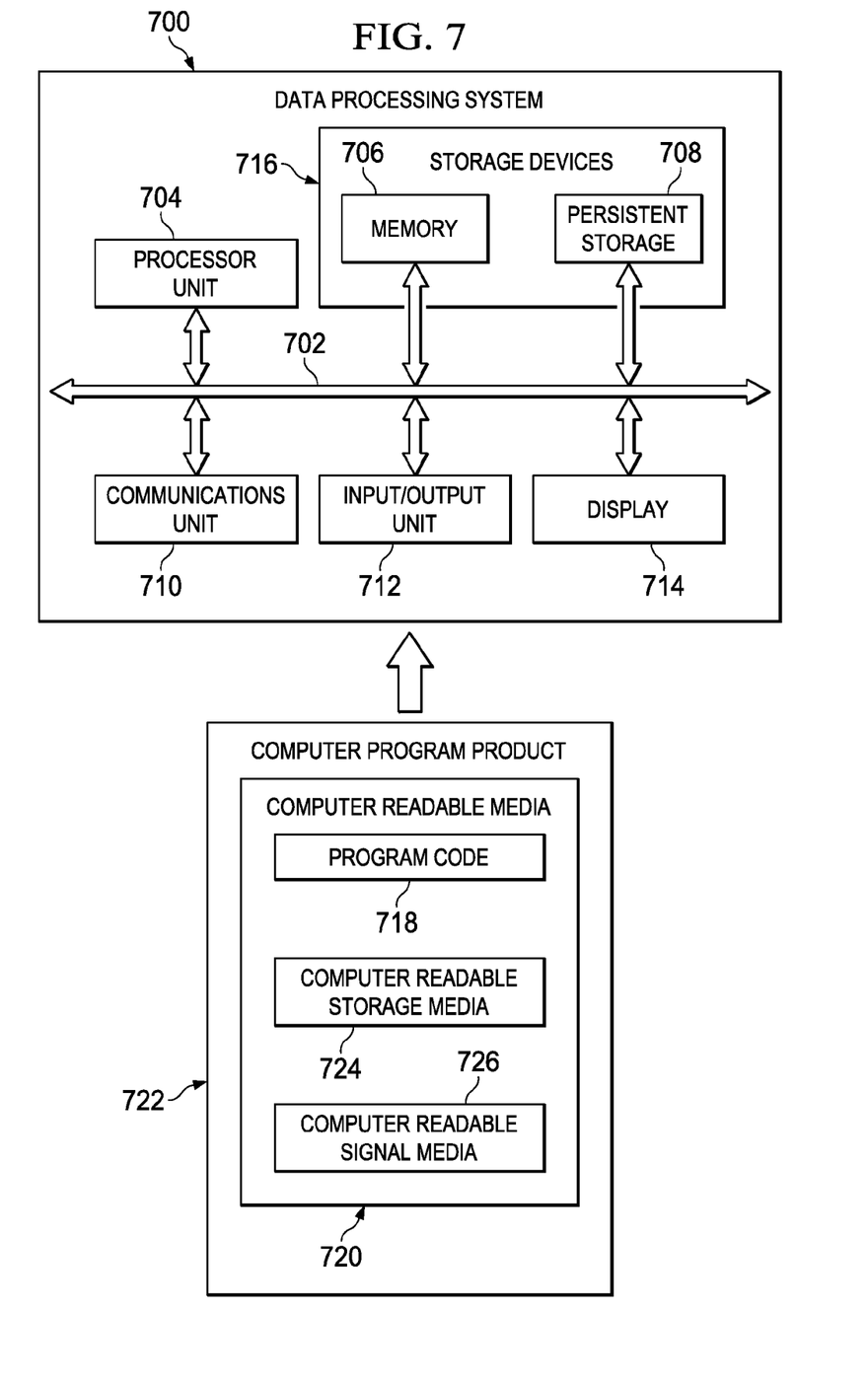
FIG. 7 is an illustration of a block diagram of a data processing system in accordance with an illustrative embodiment.

Turning now to FIG. 7, an illustration of a block diagram of a data processing system is depicted in accordance with an illustrative embodiment. Data processing system 700 may be one implementation of controller 204 of FIG. 2. Data processing system 700 may be used to implement identification of at least one of number of sending elements 230, number of inactive elements 232, and number of receiving elements 234 of FIG. 2. In some illustrative examples, data processing system 700 may be used to control sending signals by transducer array 220 of FIG. 2. In this illustrative example, data processing system 700 includes communications framework 702, which provides communications between processor unit 704, memory 706, persistent storage 708, communications unit 710, input/output (I/O) unit 712, and display 714. In this example, communications framework 702 may take the form of a bus system.

Processor unit 704 serves to execute instructions for software that may be loaded into memory 706. Processor unit 704 may be a number of processors, a multi-processor core, or some other type of processor, depending on the particular implementation.

Memory 706 and persistent storage 708 are examples of storage devices 716. A storage device is any piece of hardware that is capable of storing information, such as, for example, without limitation, data, program code in functional form, and/or other suitable information either on a temporary basis and/or a permanent basis. Storage devices 716 may also be referred to as computer readable storage devices in these illustrative examples. Memory 706, in these examples, may be, for example, a random access memory or any other suitable volatile or non-volatile storage device. Persistent storage 708 may take various forms, depending on the particular implementation.

For example, persistent storage 708 may contain one or more components or devices. For example, persistent storage 708 may be a hard drive, a flash memory, a rewritable optical disk, a rewritable magnetic tape, or some combination of the above. The media used by persistent storage 708 also may be removable. For example, a removable hard drive may be used for persistent storage 708.

Communications unit 710, in these illustrative examples, provides for communications with other data processing systems or devices. In these illustrative examples, communications unit 710 is a network interface card.

Input/output unit 712 allows for input and output of data with other devices that may be connected to data processing system 700. For example, input/output unit 712 may provide a connection for user input through a keyboard, a mouse, and/or some other suitable input device. Further, input/output unit 712 may send output to a printer. Display 714 provides a mechanism to display information to a user.

Instructions for the operating system, applications, and/or programs may be located in storage devices 716, which are in communication with processor unit 704 through communications framework 702. The processes of the different embodiments may be performed by processor unit 704 using computer-implemented instructions, which may be located in a memory, such as memory 706.

These instructions are referred to as program code, computer usable program code, or computer readable program code that may be read and executed by a processor in processor unit 704. The program code in the different embodiments may be embodied on different physical or computer readable storage media, such as memory 706 or persistent storage 708.

Program code 718 is located in a functional form on computer readable media 720 that is selectively removable and may be loaded onto or transferred to data processing system 700 for execution by processor unit 704. Program code 718 and computer readable media 720 form computer program product 722 in these illustrative examples. In one example, computer readable media 720 may be computer readable storage media 724 or computer readable signal media 726.

In these illustrative examples, computer readable storage media 724 is a physical or tangible storage device used to store program code 718 rather than a medium that propagates or transmits program code 718.

Alternatively, program code 718 may be transferred to data processing system 700 using computer readable signal media 726. Computer readable signal media 726 may be, for example, a propagated data signal containing program code 718. For example, computer readable signal media 726 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 700 are not meant to provide architectural limitations to the manner in which different embodiments may be implemented. The different illustrative embodiments may be implemented in a data processing system including components in addition to and/or in place of those illustrated for data processing system 700. Other components shown in FIG. 7 can be varied from the illustrative examples shown. The different embodiments may be implemented using any hardware device or system capable of running program code 718.

Figure 8:
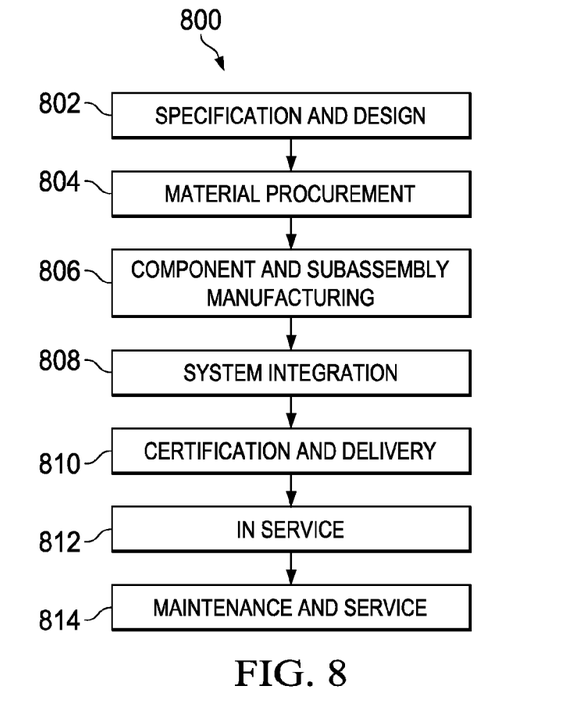
FIG. 8 is an illustration of an aircraft manufacturing and service method in the form of a block diagram in accordance with an illustrative embodiment.
Figure 9:
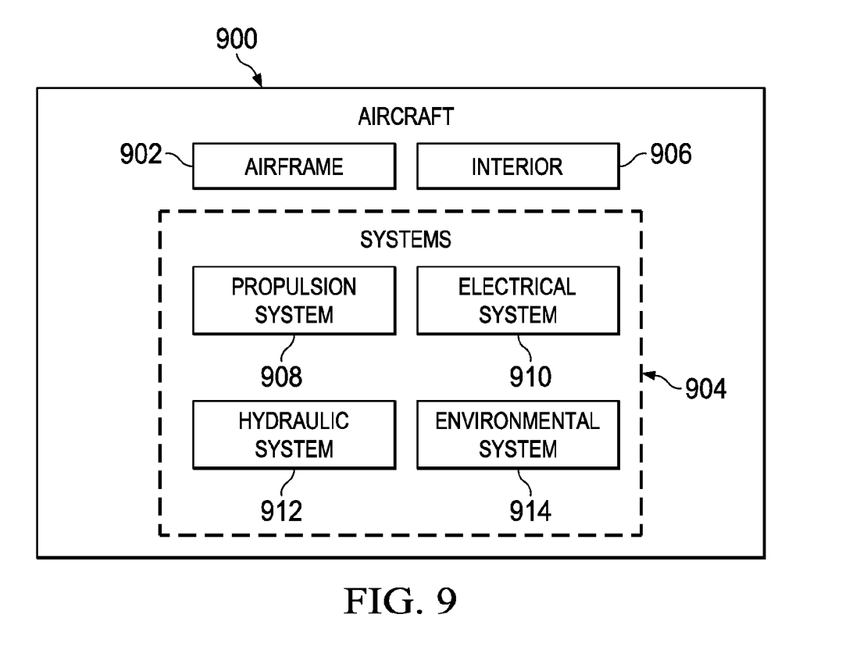
FIG. 9 is an illustration of an aircraft in the form of a block diagram in which an illustrative embodiment may be implemented.

Illustrative embodiments of the disclosure may be described in the context of aircraft manufacturing and service method 800 as shown in FIG. 8 and aircraft 900 as shown in FIG. 9. Turning first to FIG. 8, an illustration of an aircraft manufacturing and service method is depicted in the form of a block diagram in accordance with an illustrative embodiment. During pre-production, aircraft manufacturing and service method 800 may include specification and design 802 of aircraft 900 in FIG. 9 and material procurement 804.

During production, component and subassembly manufacturing 806 and system integration 808 of aircraft 900 in FIG. 9 takes place. Thereafter, aircraft 900 in FIG. 9 may go through certification and delivery 810 in order to be placed in service 812. While in service 812 by a customer, aircraft 900 in FIG. 9 is scheduled for routine maintenance and service 814, which may include modification, reconfiguration, refurbishment, and other maintenance or service.

Each of the processes of aircraft manufacturing and service method 800 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 9, an illustration of an aircraft is depicted in the form of a block diagram in which an illustrative embodiment may be implemented. In this example, aircraft 900 is produced by aircraft manufacturing and service method 800 in FIG. 8 and may include airframe 902 with plurality of systems 904 and interior 906. Examples of systems 904 include one or more of propulsion system 908, electrical system 910, hydraulic system 912, and environmental system 914. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 800 in FIG. 8. One or more illustrative embodiments may be used during component and subassembly manufacturing 806. For example, inspection equipment 206 in FIG. 2 may be used during component and subassembly manufacturing 806. Further, inspection equipment 206 may also be used to perform replacements during maintenance and service 814. For example, replacement parts for aircraft 900 may be inspected during scheduled maintenance for aircraft 900.

Thus, the different illustrative embodiments provide a method and apparatus for sending signals from a transducer array at incidence angles. In one illustrative example, signals may be sent from a transducer array at an incidence angle using electronic time-delay beam steering. In some illustrative examples, a number of inactive elements may receive response signals reflected from a number of inconsistencies in a structure.

The different illustrative embodiments may provide a method and apparatus for inspecting a structure in reduced time. The different illustrative embodiments may provide a method and apparatus for inspecting a structure with greater sensitivity to debris or other foreign materials. The different illustrative embodiments may provide a method and apparatus for providing a greater signal to noise ratio in ultrasound inspection using a transducer array.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method comprising:
    sending a signal into a structure at an incidence angle from a transducer array;
    detecting a response signal at the transducer array to form a received response, the response signal reflected from the structure in response to the signal sent into the structure; and
    identifying a first location of the transducer array, wherein the first location is an estimated receiving location for a response signal reflected from a back surface of the structure.

2. The method of claim 1, further comprising:
    configuring the transducer array such that receiving elements are located at the first location.

3. The method of claim 1 further comprising:
    determining a second location of the transducer array, wherein the second location is an estimated receiving location for a response signal reflected from an inconsistency within the structure.

4. The method of claim 3 further comprising:
    configuring the transducer array such that inactive elements are located at the second location.

5. The method of claim 1 further comprising:
    identifying an inconsistency within the structure using the response signal.

6. The method of claim 5, wherein the inconsistency comprises foreign material within the structure.

7. The method of claim 1, wherein the incidence angle is approximately 6 degrees.

8. The method of claim 1, wherein the structure comprises a composite material.

9. The method of claim 1, wherein the structure is comprised of a material selected from at least one of a metal, a composite material, a plastic, and a ceramic.

10. The method of claim 1, wherein the structure is comprised of a plurality of layers of material.

11. The method of claim 1, wherein sending the signal into the structure at the incidence angle from the transducer array comprises sending the signal into the structure at the incidence angle from the transducer array using electronic time-delay beam steering.

12. The method of claim 1, wherein identifying the first location is based on an incidence angle, a thickness, and a material velocity.

13. An apparatus comprising:
    a transducer array comprising a plurality of elements; a number of sending elements in the plurality of elements configured to send a signal into a structure at an incidence angle; and a number of receiving elements in the plurality of elements configured to detect a response signal reflected from a back surface of the structure, wherein the number of receiving elements is located at a first location, wherein the first location is an estimated receiving location for the response signal reflected from the back surface of the structure.

14. The apparatus of claim 13, further comprising:
a number of inactive elements in the plurality of elements located between the number of sending elements and the number of receiving elements.

15. The apparatus of claim 14, wherein the number of inactive elements is located at a second location, wherein the second location is an estimated receiving location for a response signal reflected from an inconsistency within the structure.

16. The apparatus of claim 15, wherein the number of inactive elements is configured to decrease an amplitude of the response signal reflected from the back surface of the structure when an inconsistency is present.

17. The apparatus of claim 13, wherein the incidence angle is configured to decrease an amplitude of the response signal reflected from the back surface of the structure when an inconsistency is present.

18. The apparatus of claim 13 further comprising:
electronic time-delay beam steering usable with the sending elements to send the signal into the composite material at the incidence angle.

19. A method comprising:
identifying a first location of a transducer array based on an incidence angle, a thickness, and a material velocity;
identifying a second location of the transducer array based on the incidence angle, the thickness, and the material velocity;
configuring the transducer array using the first location and the second location, in which configuring the transducer array comprises configuring the transducer array to have receiving elements at the first location and configuring the transducer array to have inactive elements at the second location;
sending a signal into a composite material at the incidence angle using sending elements of the transducer array;
detecting a response signal reflected from a back surface of the composite material using the receiving elements; and
identifying an inconsistency within the composite material using the response signal.

20. The method of claim 19, wherein sending the signal into the composite material at the incidence angle using the sending elements of the transducer array comprises sending the signal into the composite material at the incidence angle using the sending elements of the transducer array and electronic time-delay beam steering.

21. A method comprising:
sending a signal into a structure at an incidence angle from a transducer array;
detecting a response signal at the transducer array to form a received response, the response signal reflected from the structure in response to the signal sent into the structure; and
determining a second location of the transducer array, wherein the second location is an estimated receiving location for a response signal reflected from an inconsistency within the structure.

22. The method of claim 21 further comprising:
configuring the transducer array such that inactive elements are located at the second location.

23. An apparatus comprising:
a transducer array comprising a plurality of elements; a number of sending elements in the plurality of elements configured to send a signal into a structure at an incidence angle; and a number of receiving elements in the plurality of elements configured to detect a response signal reflected from a back surface of the structure; and
a number of inactive elements in the plurality of elements located between the number of sending elements and the number of receiving elements, wherein the number of inactive elements is located at a second location, wherein the second location is an estimated receiving location for a response signal reflected from an inconsistency within the structure.

24. The apparatus of claim 23, wherein the number of inactive elements is configured to decrease an amplitude of the response signal reflected from the back surface of the structure when an inconsistency is present.

25. A method comprising:
identifying a first location of a transducer array based on an incidence angle, a thickness, and a material velocity;
identifying a second location of the transducer array based on the incidence angle, the thickness, and the material velocity;
configuring the transducer array using the first location and the second location, in which configuring the transducer array comprises configuring the transducer array to have receiving elements at the first location and configuring the transducer array to have inactive elements at the second location;
sending a signal into a composite material at the incidence angle using sending elements of the transducer array;
detecting a response signal reflected from an inconsistency within the composite material using the receiving elements; and
identifying an inconsistency within the composite material using the response signal.

26. The method of claim 25, wherein sending the signal into the composite material at the incidence angle using the sending elements of the transducer array comprises sending the signal into the composite material at the incidence angle using the sending elements of the transducer array and electronic time-delay beam steering.

* * * * *